United States Patent
Li

(10) Patent No.: US 6,830,833 B2
(45) Date of Patent: Dec. 14, 2004

(54) ORGANIC LIGHT-EMITTING DEVICE BASED ON FUSED CONJUGATED COMPOUNDS

(75) Inventor: Xiao-Chang Charles Li, Union City, CA (US)

(73) Assignee: Canon Kabushiki Kaisha, Tokyo (JP)

(*) Notice: Subject to any disclaimer, the term of this patent is extended or adjusted under 35 U.S.C. 154(b) by 2 days.

(21) Appl. No.: 10/308,099

(22) Filed: Dec. 3, 2002

(65) Prior Publication Data

US 2004/0106004 A1 Jun. 3, 2004

(51) Int. Cl.⁷ .......................... H05B 33/14; C09K 11/06
(52) U.S. Cl. .................. 428/690; 428/917; 313/504; 313/506; 546/41; 556/431; 556/432; 564/426; 564/429
(58) Field of Search .................. 428/690, 917; 313/504, 506; 528/408; 556/410, 413, 431, 432, 465; 546/38, 41

(56) References Cited

U.S. PATENT DOCUMENTS

| | | | |
|---|---|---|---|
| 5,026,894 A | 6/1991 | Tour et al. | 558/46 |
| 5,621,131 A | 4/1997 | Kreuder et al. | 558/46 |
| 5,763,636 A | 6/1998 | Kreuder et al. | 528/46 |
| 5,840,217 A * | 11/1998 | Lupo et al. | 252/583 |
| 5,859,211 A | 1/1999 | Kreuder et al. | 528/403 |
| 5,942,340 A | 8/1999 | Hu et al. | 428/690 |
| 5,981,773 A * | 11/1999 | Langhals et al. | 549/381 |
| 6,004,685 A | 12/1999 | Antoniadis et al. | 428/690 |
| 6,132,641 A | 10/2000 | Rietz et al. | 252/301.16 |
| 6,169,163 B1 * | 1/2001 | Woo et al. | 528/397 |
| 6,329,082 B1 | 12/2001 | Kreuder et al. | 428/690 |
| 6,361,884 B1 | 3/2002 | Kreuder et al. | 428/690 |
| 6,376,694 B1 | 4/2002 | Uchida et al. | 556/406 |
| 6,416,887 B1 * | 7/2002 | Tokito et al. | 428/690 |
| 6,664,396 B1 * | 12/2003 | Cosimbescu | 546/41 |

FOREIGN PATENT DOCUMENTS

| | | | |
|---|---|---|---|
| EP | 1363980 | * | 11/2003 |
| JP | 5-202355 | | 8/1993 |
| JP | 2002237384 | * | 8/2002 |

OTHER PUBLICATIONS

U.S. Patent Application Publication No. US 2002/0048686.
Handbook of Chemistry and Physics, 62d Edition (1981–2), CRC Press, pp. C–23 through C–25.

* cited by examiner

Primary Examiner—Rena L. Dye
Assistant Examiner—Camie Thompson
(74) Attorney, Agent, or Firm—Fitzpatrick, Cella, Harper and Scinto

(57) ABSTRACT

Fused conjugated polymers having the following general formula

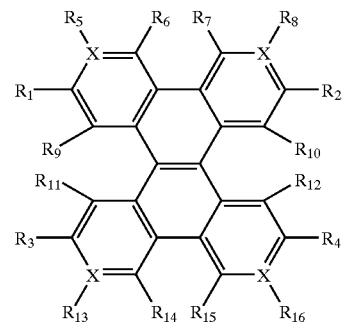

wherein X=C or N; $R_1$–$R_{16}$ is independently selected from H, D, alkyl, alkoxyl, silyl, aromatic ring, fused aromatic ring, heteroaromatic ring, fused heteroaromatic ring, diarylamino group, carbazole, and at least one of them being a crosslinkable group consisting of a vinyl double bond or an azide group are useful in the fabrication of organic light emitting devices.

12 Claims, 2 Drawing Sheets

Three dimensional structure of 4

The chemical structure of 4 and its three dimensional geometry showing the spiro-type feature.

Three dimensional structure of 4

Figure 1: The chemical structure of 4 and its three dimensional geometry showing the spiro-type feature.

Figure 2: Electroluminescence spectrum (EL) and photoluminescence spectrum of compound 12.

ORGANIC LIGHT-EMITTING DEVICE BASED ON FUSED CONJUGATED COMPOUNDS

BACKGROUND OF THE INVENTION

1. Field of the Invention

The present invention relates to an organic light emitting device (OLED) in which a fused compound or its derivatives are used as the emissive layer and/or one or more of the charge transport layers, or as a host material in an OLED.

2. Description of the Related Art

Electroluminescence materials are materials which are capable of radiating light on application of an electric field. The physical model for describing this effect is based on the radiative recombination of electrons and electron gaps (holes). In light-emitting diodes, the charge carriers are injected via the cathode or anode into the electroluminescence material. Electroluminescence devices comprise a luminescence material as a light-emitting layer.

Significant efforts have been expended in developing suitable electroluminescence materials for use in organic light emitting devices (OLEDs). Such devices are commercially attractive because they offer the promise of low-cost fabrication of high-density pixeled displays exhibiting bright electroluminescence with long life times and wide color range.

A simple OLED is fabricated by sandwiching an emissive layer between an anode and a cathode. When a bias is applied across the electrodes, holes and electrons are respectively injected from the anode and cathode into the emissive layer, typically facilitated by hole transport and electron transport layers adjacent to the respective electrodes. The holes and electrons radiatively combine in the emissive layer and emit light. Improved performance can be obtained if blocking layers are provided to block against the injection of either holes or electrons from the adjoining layer and their subsequent escape from the device. As further examples, a double-layered structure is fabricated from a combined hole-injecting and transporting layer together with a combined electron-transporting and light-emitting layer. Likewise, a triple-layered structure is compose of a hole-injecting and transporting layer, a light-emitting layer, and an electron-injecting and transporting layer.

In addition, it is possible to form these layers from a host material doped with another material designed to achieve the desired effect of the layer (for example, to achieve a hole transport effect, an electron transport effect, or an emissive effect).

Some of these layers can be combined, such as devices which obtain electroluminescence through doping of an electron transport layer with flourescent dye materials.

Because of consumer expectations of good efficiency, long lifetime and pure color for OLEDs, a need exists for development of suitable materials for the various layers. The desired material used for OLED should ideally combine the following properties: 1) Suitable conjugation to meet band gap requirements for optimal charge injection and color requirements; 2) Easy processability for thin film formation with good morphology; 3) High thermal stability; 4) Long-term stability during device operation and in storage.

Conjugated polymer semi-conductors have attracted attention for optoelectronic applications that traditionally have been the domains of inorganic semi-conductors. The structural flexibility, the very low cost for processing, and the flexible thin film features of conjugated polymers make organic semi-conductive polymer devices competitive with the inorganic semi-conductors. Most conjugated polymers are highly luminescent, and they have attracted great attention in light-emitting device applications.

Many fused aromatic compounds can basically meet the above requirements, but they have low solubility and are difficult to prepare and purify. One way to solve the solubility problem is the use of a spiro configuration.

Spiro compounds are compounds in which two ring systems are linked via a single tetravalent atom. The tetravalent atom is referred to as the spiro atom. Handbook of Chemistry and Physics, 62d Edition (1981–2), CRC Press, pages C-23–C-25. The basic structure of the spiro atom compound can be generally illustrated by 1, below.

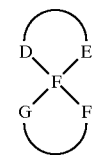

A typical example of a spiro compound is shown below as compound 2.

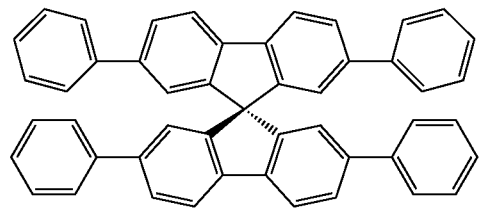

Most spiro compounds are very soluble even with a long conjugated aromatic ring system.

Spiro compounds are known to be luminescent and their use in light emitting devices has been suggested.

For example, U.S. Pat. No. 5,621,131 suggests polymers of a monomer having a spiro structure as an electroluminescent material.

U.S. Pat. No. 5,026,894 relates to a spiro compound with a defined physical structure for use in forming semiconducting polymers with perpendicularly arranged cores. The compounds with perpendicularly arranged cores could then be used in memory, logic and amplification computing systems.

U.S. Pat. No. 5,763,636 asserts that certain conjugated polymers having a plurality of spiro atoms are particularly suitable as electro-luminescence materials. These polymers are highly complex, with many possible substituents.

Conjugated polymers comprising at least one unit based on a heterospiro framework have been alleged to have good properties including good electroluminescence, photoluminescence and high color purity. U.S. Pat. Nos. 5,859,211; 6,329,082.

Polymers of substituted and unsubstituted 9,9'-spirobisfluorenes are recommended for use in light-emitting diodes or electrodes in display applications. Such compounds are said to be blue-fluorescing polymers which are soluble in many solvents and therefore readily applied by conventional coating processes. U.S. Pat. No. 6,132,641. Similar polymeric compounds are also described in U.S. Pat. No. 5,840,217.

Spiro compounds have thus been recommended for use in electronic displays as indicated above. Those prior art compounds have the characteristics of high luminescence, good solubility and excellent color purity due to the prevention of intermolecular aggregation. Such compounds can be actually regarded as the combination of two chromophores being crossed-over each other. However, the non-conjugated spiro atom can also break up the long conjugation and lead to an inferior charge injection property. Further, the good solubility can lead to deterioration over time due to changes in morphology during normal operating conditions or during conditions of elevated temperatures.

This invention relates to electroluminescence materials suitable for use in light-emitting devices and flat-panel displays, and methods of using the same material. Particularly, this invention is aimed to improve the charge injection property of spiro-atom linked luminescent materials.

SUMMARY OF THE INVENTION

This invention relates to electroluminescence materials suitable for use in light-emitting devices and flat-panel displays, and methods of using the same material. Particularly, this invention is aimed to improve the charge injection property of spiro-atom linked luminescent materials.

To enhance the charge injection ability while maintaining the non-planar configuration of a spiro compound, it has now been found that an excellent approach is to use a conjugated double bond to bond the two ring system, to form fused aromatic compound as illustrated in 3:

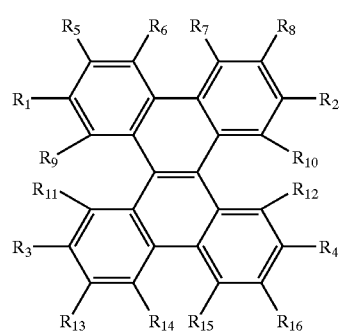

The above compound 3 does not have a spiro atom as defined above, but rather a vinyl-linking two ring system in a non-planar geometry. This type of compound is a fused compound and can be regarded as a quasi-spiro compound. It has excellent hole transport properties as well as good emissive characteristics. However, its good solubility has a drawback if it is used for a hole transport layer followed with a solution thin film deposition method, such as ink-jet printing and spin-coating technique as the following solution process may damage the hole transport layer. However, this shortcoming can be overcome by cross-linking the fused compounds before or after they have been applied to the desired substrate.

In a further aspect, the present invention is an organic light emitting device, an organic solid state laser, and a method for producing such devices, comprising a transparent electrode; a cathode; and an active layer containing a luminescent polymer according to the present invention.

In a still further aspect, the present invention is a photovoltaic cell, and a method for producing such a cell, comprising an active layer containing a luminescent polymer according to the present invention.

In another aspect, the present invention is an electrochromic display, and a method for producing such a display, comprising an active layer containing a luminescent polymer according to the present invention.

This brief summary has been provided so that the nature of the invention may be understood quickly. A more complete understanding of the invention can be obtained by reference to the following detailed description of the preferred embodiment thereof in connection with the attached drawings.

DETAILED DESCRIPTION OF THE INVENTION

It is an object of the invention to provide an improved OLED in which fused conjugated compounds are used as the emissive layer and/or one or more of the charge transport layers, or as a host material for one or more of such layers.

This invention is related to electroluminescent devices wherein one of the layers is composed of a fused compound with the general formula illustrated in 4. The device has an advantage of good charge transport and high efficiency, as well as long-life time.

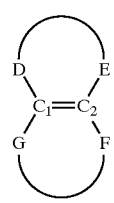

Figure 1:
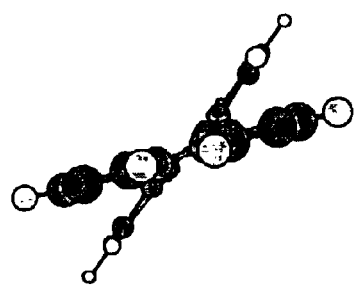
FIG. 1 is a representation of the three dimensional configuration of the fused conjugated compounds of the invention.

In formula 4 noted above, the ring system of C1-C2-E-D, or C1-C2-G-F is a ring of 5–8 member ring containing C, O, S, N, P, Se, and a cross-linkable functional group. Due to the bond twist nature, the two-ring system is non-planar. FIG. 1 shows the geometry of the compound 4. Therefore, the vinyl double bond can combine a two ring system chromophore in a spiro-type configuration so as to make the two ring systems non-planar to enhance solubility (good for preparation and purification and solution processing) of the compound, and to electronically enhance charge transport ability by linking two conjugated ring systems with a conjugated double bond.

Selecting ring constituent atoms from C, O, S, N, P, Se, can adjust electron affinity to balance the charge injection and transport ability of the material. For instance, the electron negativity increases in the order $CR<N<NR^+<O^+$. Therefore, quinoline has a better electron affinity than naphthalene.

The attachment of a cross-linkable group to the fused compound of the present invention provides a post-treatment to render the thin film insoluble. This can be beneficial to chemically fix the morphology of the formed thin film, to facilitate layer-by-layer sequential solution processing of thin films one layer on top of previous layer, and to increase thermal stability of the device.

Preferably, the general structure is illustrated as in formula 5:

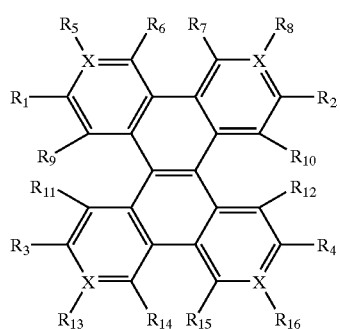

where X=C or N; $R_1$–$R_{16}$ is independently selected from H, D, alkyl, alkoxyl, silyl, aromatic ring, fused aromatic ring, heteroaromatic ring, fused heteroaromatic ring, diarylamino group, carbazole, and at least one of them being a crosslinkable group consisting of a vinyl double bond or an azide group.

Examples of $R_1$–$R_{16}$ are presented in Scheme 1:

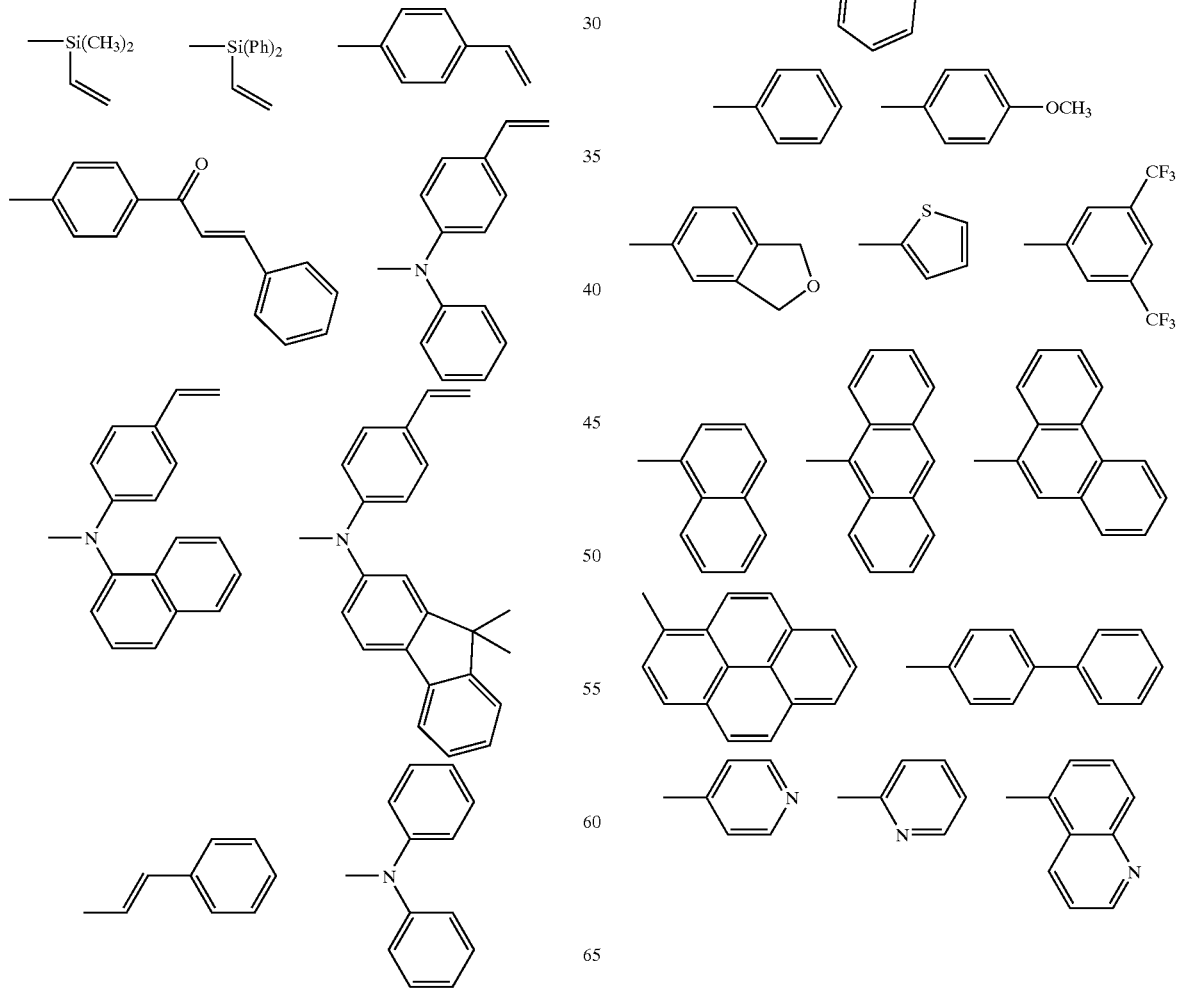

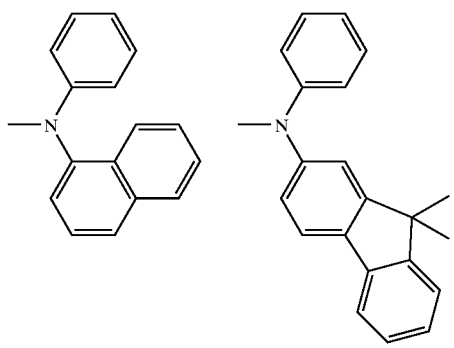

The compounds according to the invention have a conjugated spiro-type linkage linking two chromophores or two polymers together, and the spiro-type linkage renders the two chromophores or two polymers crossed over each other, so as to effectively prevent the intermolecular pi-conjugation system from forming an aggregate. The conjugated spiro system also allows electronic interaction between the two crossed systems.

The compound expressed according to formula (5) can be used directly as a charge transport layer, as an emissive layer, or can be used as a host material in OLEDs. Assembly of such OLED's is well known to those of ordinary skill in the art.

Fabrication of a suitable hole transport layer of the compound (5) can be accomplished through use of thermal deposition in a vacuum, or by a solution thin film deposition techniques, such as spin coating of a solution, or ink-jet printing. Thus, a hole-transport layer coated ITO glass substrate can be heated to a suitable temperature between 80 to 240° C. in order to induce a cross-linking reaction. The double bond in the compound 5 will meet with another double bond of another compound 5 molecule and via 2+2 cyclization, lead to the formation of an insoluble network which will not be damaged or altered by further processing.

Crosslinking reaction of the chromophore under heating condition (temperature range from 150–350 C, preferably between 180–250 C).

Fused conjugated compounds of the present invention can be synthesized in accordance with the following example:

EXAMPLE 1

Preparation of a Cross-Linkable Hole Transport Compound 11

The synthesis of compound 11 was prepared according to Scheme 2:

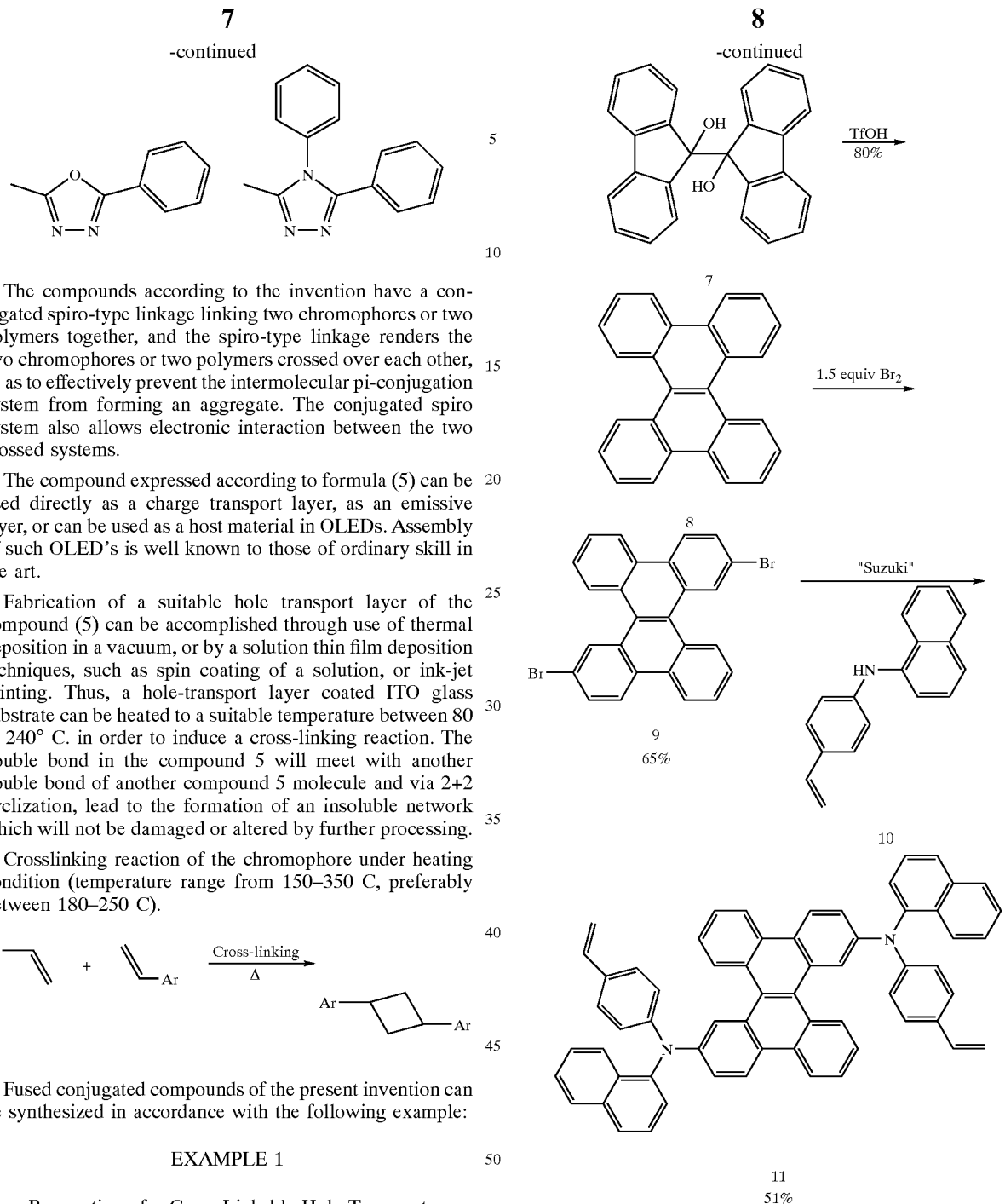

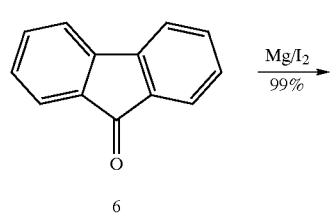

Magnesium iodide (17.0 g, 61.1 mmol) and magnesium turnings (4.0 g, 160.5 mmol) were charged into a 500 ml two-neck flask. The system was degassed and filled with nitrogen. Anhydrous benzene (150 ml) and ether (50 ml) were added into the flask with a syringe under nitrogen. Fluorenone (18.0 g, 100 mmol) was the added portion by portion at room temperature. The suspension was stirred for 10 hours, and water (20 ml) was added to terminate the reaction. The crude solid was digested with hot alcohol (15 ml) to remove traces of the ketone. The crude product was recrystallized from chloroform/hexane to afford white powder product 7 (11.8 g, 66%). FT-IR and GC/MS proved the product.

The alcohol 7 (8.629 g, 47.36 mmol) was dissolved in anhydrous benzene (170 ml) under mild heating. After the system was cooled to room temperature, trifluoromethane sulfonic acid (28 ml) was added. The red solution was stirred overnight (16 hours) and then poured into ice water to give a white precipitate. The crude product was recrystallized from ether/hexane to afford a white powder 8 (4.5 g, 59%). FT-IR and GC/MS proved the product. $T_m=201°$ C.

The compound 8 (2.098 g, 6.388 mmol) was dissolved in dichloromethane (25 ml), and catalytic iodine (16.2 mg, 0.0688 mmol) was added into the solution. Bromine (2.09 g, 13.09 mmol) was added into the solution within 30 min. at 0° C. The mixture was stirred for 18 hours, and potassium hydroxide (10 ml, 20% solution) was added into the mixture to terminate the reaction. The mixture was poured into methanol (300 ml) to give a white precipitate. The solid was filtered and washed by water (2×80 ml), methanol (2×30 ml) and dried under vacuum. GC/MS revealed to be the product 9 (2.733 g, 88% yield).

Compound 9 (0.300 g, 0.617 mmol), tris(dibenzylideneacetone)dipalladium [Pd2(dba)3](8.47 mg, 0.00926 mmol) and bis(diphenylphosphine)ferrocene (DPPF) (7.7 mg, 0.01388 mmol) were charged into a 50 ml two-neck flask. The system was degassed and filled with nitrogen. Anhydrous toluene (10 ml) was added to dissolve the solid. After stirring for 10 min., sodium tert-butoxide (77.1 mg, 0.802 mmol) was added, and followed with the addition of naphthalene-1-yl-(4-vinyl-phenyl)-amine 10 (0.333 g ,1.357 mmol). The mixture was heated to 90° C. and stirred for 24 hours. The mixture was poured into methanol (80 ml) to give an off-white precipitate. The compound was purified by silicon flash column by using hexane and hexane/dichloromethane (5:1, v/v). The final product 11 was obtained as a light yellow powder (0.26 g, 51% yield). Thermal analysis reveal that its Tm>280° C.

Compound 11(15 mg) was dissolved in chloroform (0.8 ml) and the solution was spin-coated on to a glass substrate to form a 30 nm thin film. The glass substrate was heated under vacuum to 180° C. for 4 hours to cross-link 11. After cooling to room temperature, the cross-linked 11 was no longer soluble in chloroform and toluene.

EXAMPLE 2

Preparation of a Cross-Linkable Emissive Compound

The compound 9 (0.606 g, 1.357) was dissolved in anhydrous tetrahydrofuran (10 ml) and degassed. After cooling to −70° C. (dry ice+acetone as cold bath), ᵗBuLi (3.19 ml in 1.7 M solution in heptane, 5.43 mmol). The red solution was stirred at −70° C. for 1.5 hours, and dimethyl vinylsilane chloride (0.327 g, 2.714 mmol) was added. The mixture was stirred and warmed to room temperature. After 14 hours stirring at room temperature, it was poured into water (300 ml). The product 12 was purified by standard silicon flash column to give yellow powder. (60% yield) The compound was characterized by FT-IR and GC/MS.

Compound 12(15 mg) was dissolved in chloroform (0.8 ml) and the solution was spin-coated on a glass substrate to form a 30 nm thin film. The glass substrate was heated under vacuum to 180° C. for 4 hours to cross-link 12.

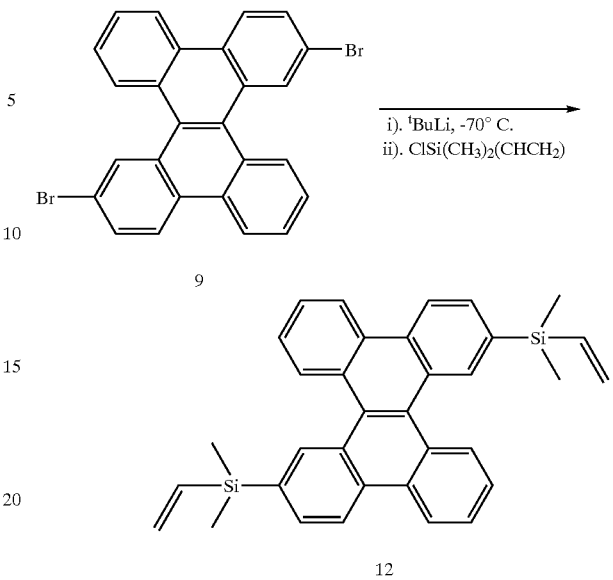

Scheme 3: Preparation of Emissive Compound 12.

EXAMPLE 3

OLED Device

Figure 2:
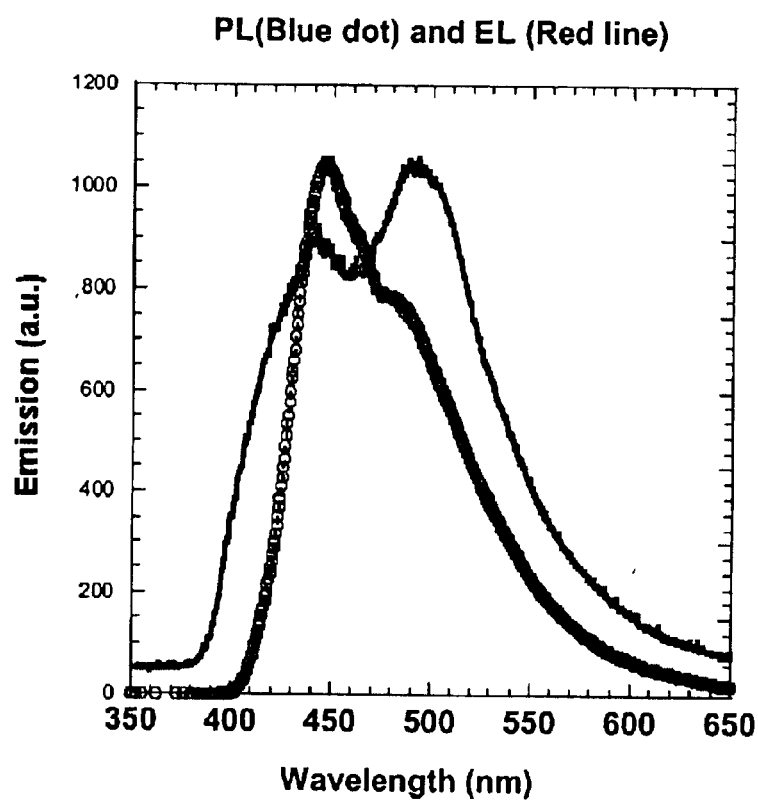
FIG. 2 shows the electroluminescence spectrum and the photoluminescence spectrum of a compound in accordance with the present invention.

The hole transport material 11 (8 mg) was dissolved in chloroform (1 ml) and filtered through a 0.5 μm Teflon membrane filter. The solution was spin-coated on a clean indium tin oxide glass substrate (ITO glass) to form a thin film 10 nm thick. The coated ITO glass was heated to 180° C. under vacuum for 4 hours. On top of the cross-linked 11, emissive compound 12 (15 mg in 0.8 ml chloroform) was spin-coated on top of the cross-linked 11 to form a thin film 30 nm thick of compound 12. The coated ITO substrate was then put into a vacuum deposition bell jar to deposit cathode metal layer, LiF (0.8 nm) followed with aluminum (150 nm). The device was further heat treated at 180° C. for 2 hours and encapsulated by epoxy resin. This device showed blue electroluminescence when it was forward biased at a voltage of 2.8 V (105 cd/m2). FIG. 2 shows the electroluminescence spectrum (EL) and photoluminescence spectrum (PL) of the compound 12.

It is expected that the above solution processing of OLED can be processed by inkjet printing, stamping, or screen printing etc.

What I claim is:

1. A fused conjugated compound having the formula

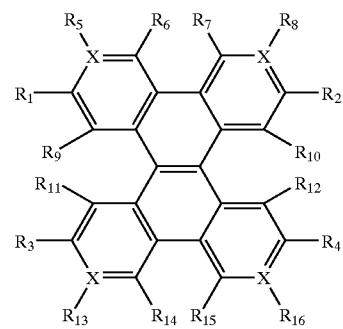

wherein X=C; $R_1$–$R_{16}$ is independently selected from H, D, alkyl, alkoxyl, silyl, aromatic ring, fused aromatic ring, heteroaromatic ring, fused heteroaromatic ring, diarylamino group, carbazole, and at least one of them being a crosslinkable group consisting of a vinyl double bond or an azide group; and R₂ and R₃ are

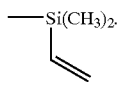

2. The fused conjugated compound according to claim 1 wherein $R_1$ and $R_4$ to $R_{16}$ are selected from

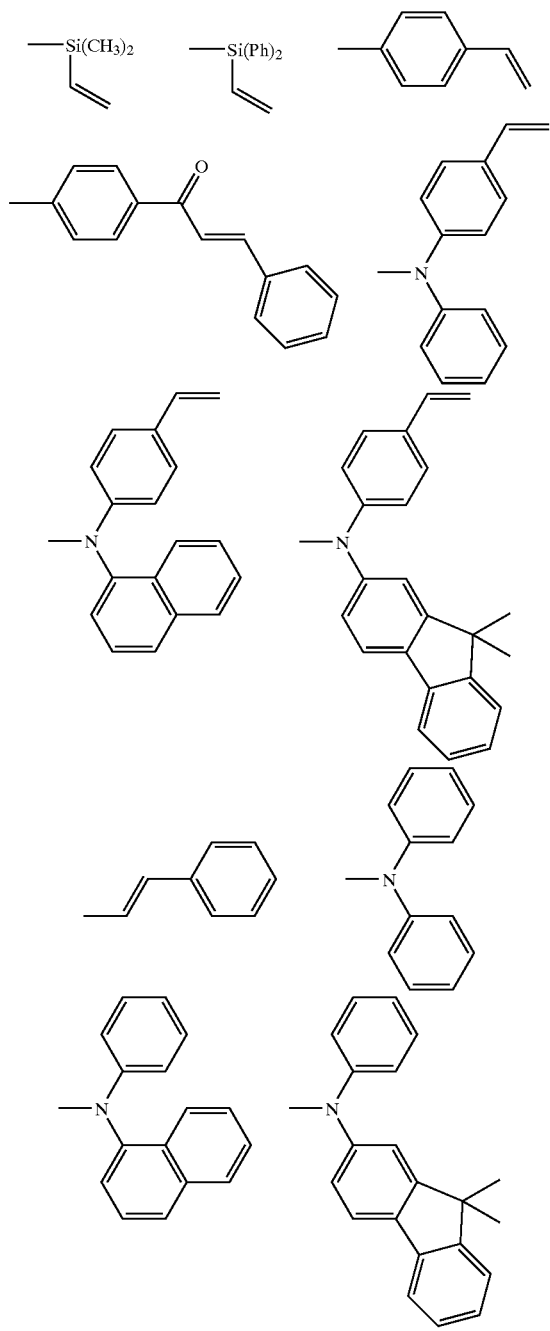

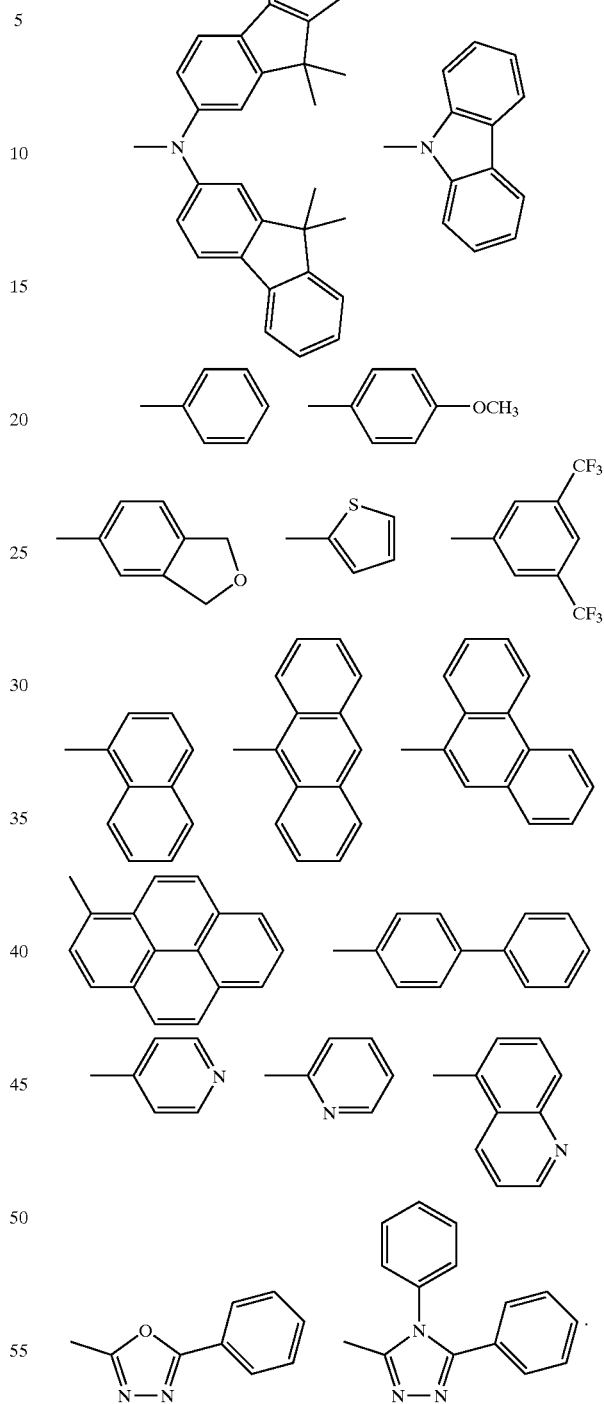

3. An organic light emitting device comprising:

an emissive layer sandwiched between at least a cathode and an anode, wherein the emissive layer includes a fused conjugated compound expressed according to the following general formula:

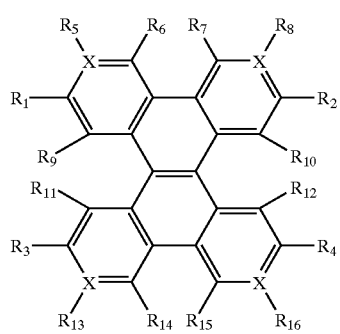

wherein X=C; $R_1$–$R_{16}$ is independently selected from H, D, alkyl, alkoxyl, silyl, aromatic ring, fused aromatic ring, heteroaromatic ring, fused heteroaromatic ring, diarylamino group, carbazole, and at least one of them being a crosslinkable group consisting of a vinyl double bond or an azide group; and $R_2$ and $R_3$ are

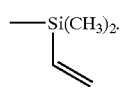

4. The organic light emitting device according to claim 3 wherein $R_1$ and $R_4$ to $R_{16}$ are selected from H, D, Br, Cl, I, $CH_3$, $NH_2$, $OCH_3$, $Si(CH_3)_3$

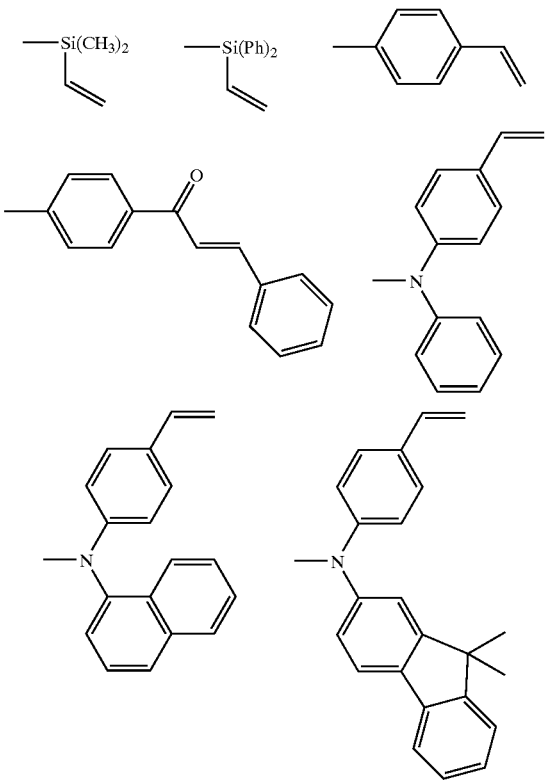

-continued

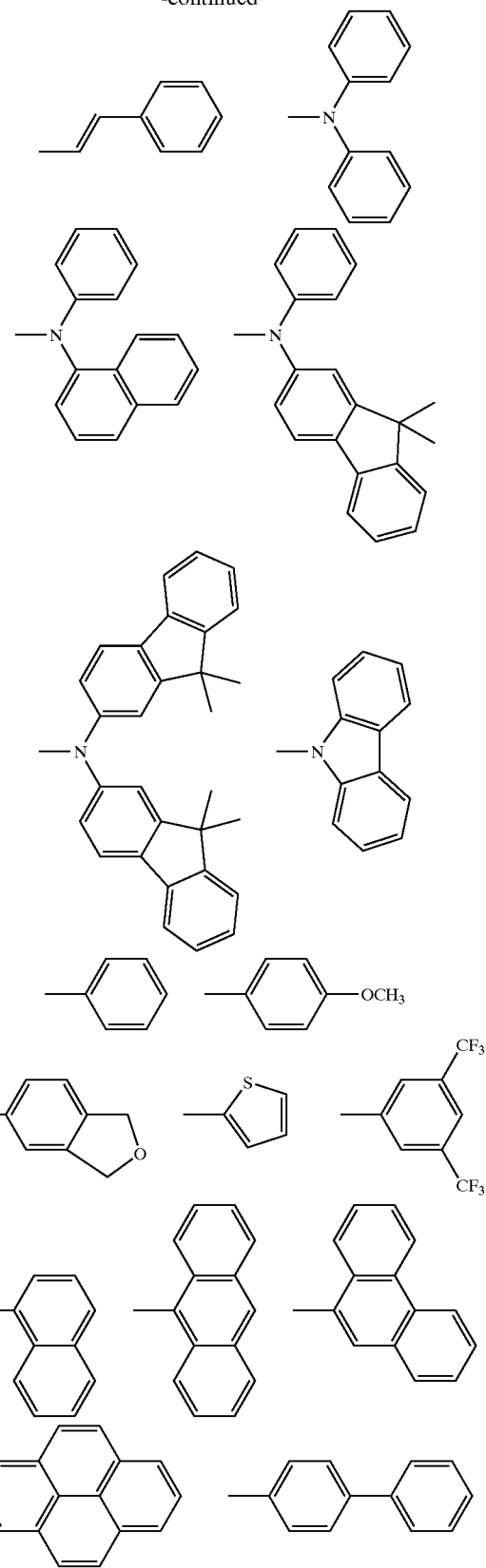

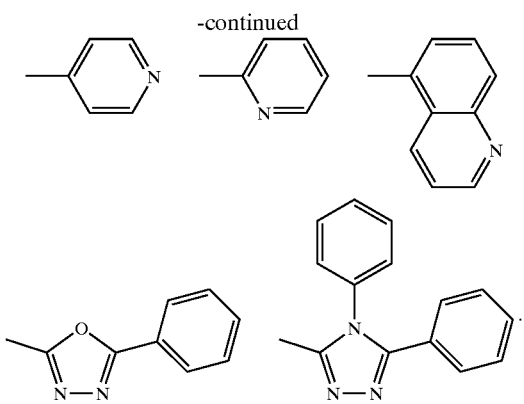

5. An organic light emitting device comprising:

an emissive layer sandwiched between at least one change transport layer and an anode and a cathode, wherein the charge transport layer includes a fused conjugated compound according to the following general formula:

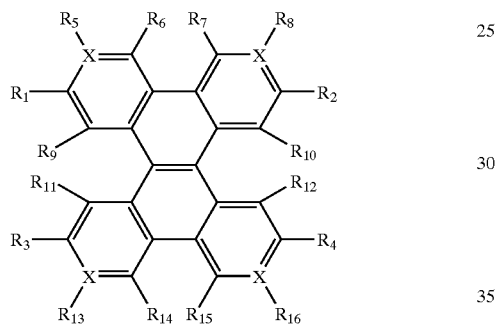

wherein X=C; $R_1$–$R_{16}$ is independently selected from H, D, alkyl, alkoxyl, silyl, aromatic ring, fused aromatic ring, heteroaromatic ring, fused heteroaromatic ring, diarylamino group, carbazole, and at least one of them being a crosslinkable group consisting of a vinyl double bond or an azide group; and $R_2$ and $R_3$ are

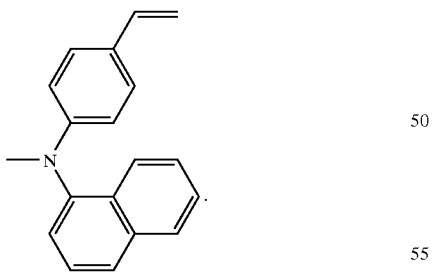

6. The organic light emitting device according to claim 5 wherein $R_1$ and $R_4$ to $R_{16}$ are selected from H, D, Br, Cl, I, $CH_3$, $NH_2$, $OCH_3$, $Si(CH_3)_3$

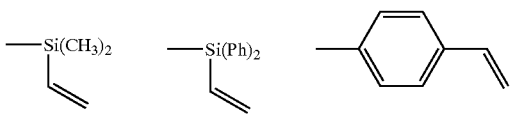

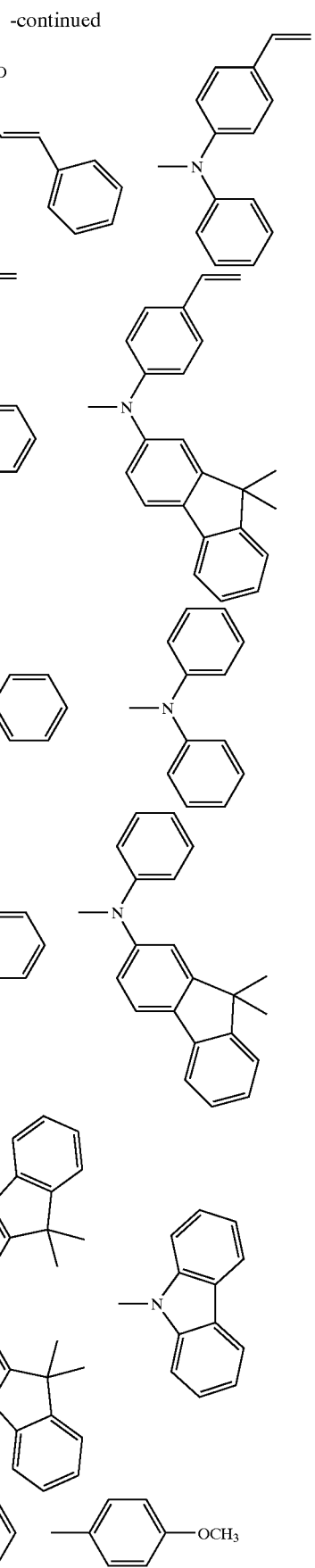

-continued

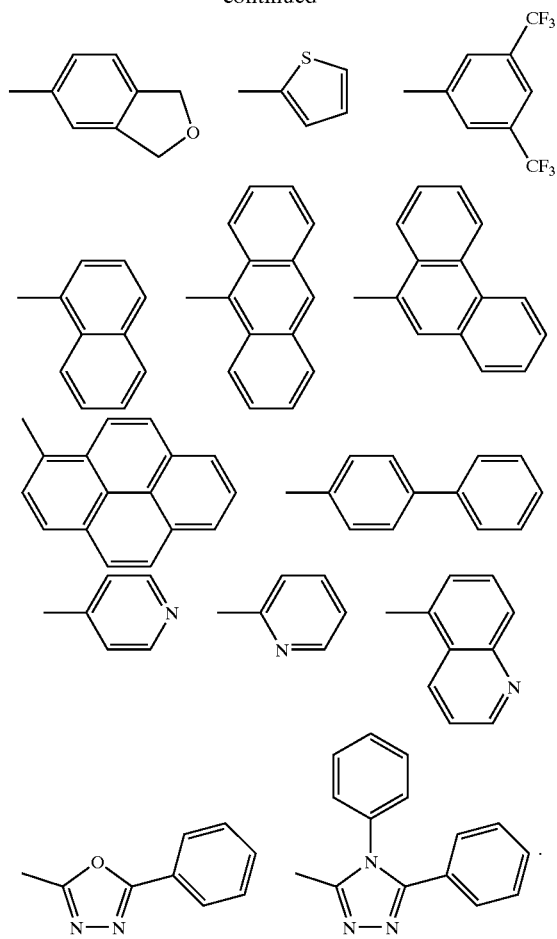

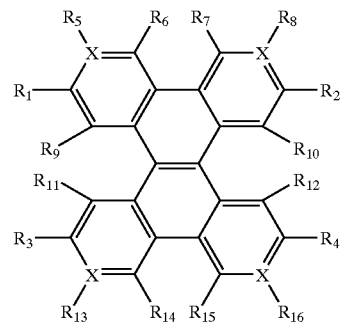

7. The organic light emitting device according to claim 3 wherein the fused conjugated compound is cross-linked.

8. The organic light emitting device according to claim 5 wherein the fused conjugated compound is cross-linked.

9. The fused conjugated compound according to claim 1 wherein the compound is cross-linked.

10. A fused conjugated compound having the formula

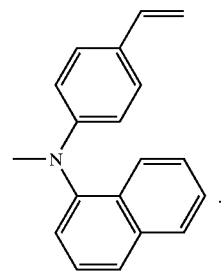

wherein X=C; $R_1$ to $R_{16}$ are independently selected from H, D, alkyl, alkoxyl, silyl, aromatic ring, fused aromatic ring, heteroaromatic ring, fused heteroaromatic ring, diarylamino group, carbazole, and at least one of them being a crosslinkable group consisting of a vinyl double bond or an azide group; and $R_2$ and $R_3$ are

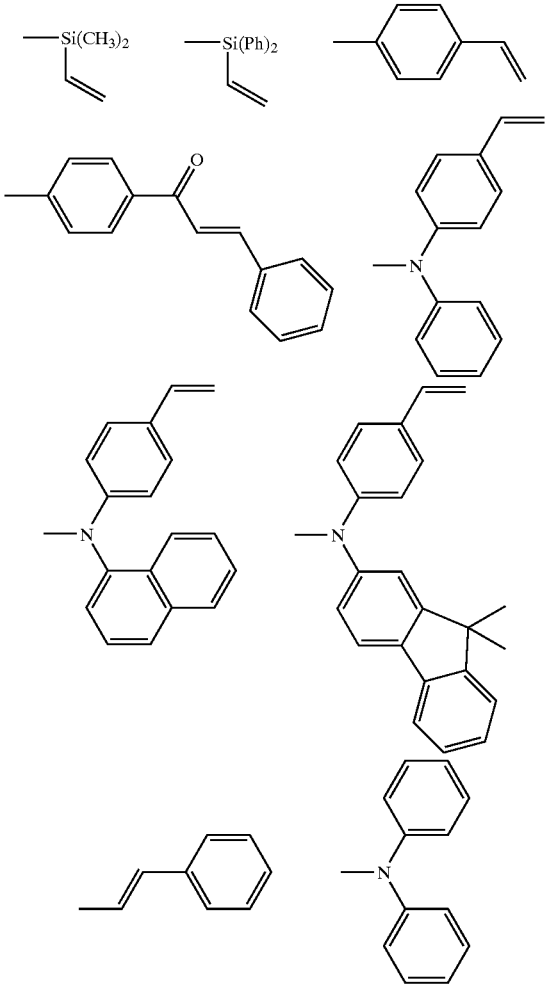

11. The fused conjugated compound according to claim 10 wherein $R_1$ and $R_4$ to $R_{16}$ are selected from H, D, Br, Cl, I, $CH_3$, $NH_2$, $OCH_3$, $Si(CH_3)_3$

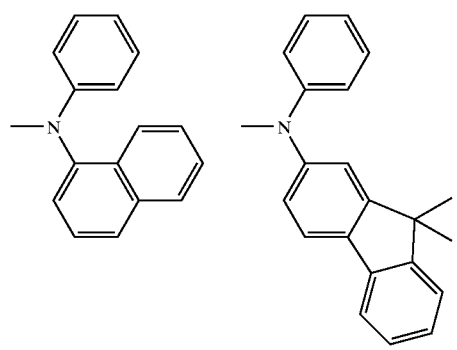
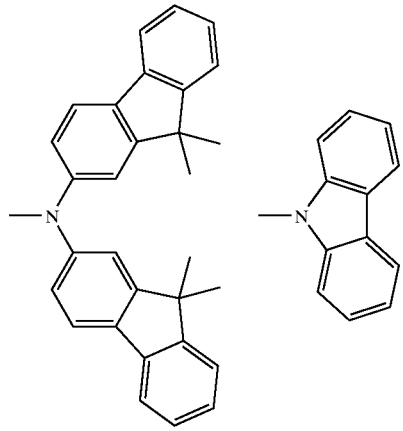
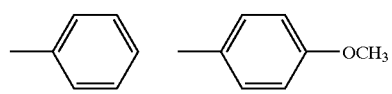
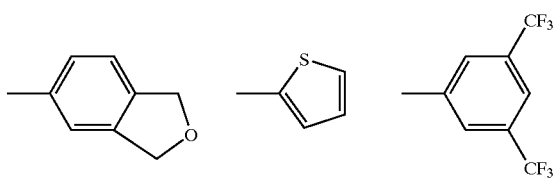
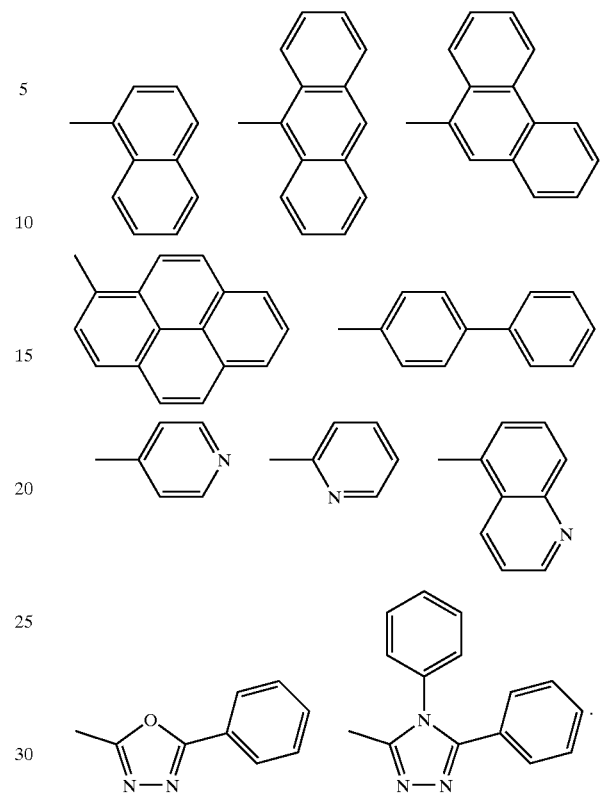
12. The fused conjugated compound according to claim 10 wherein the compound is cross-linked.
* * * * *